(12) United States Patent
Heasman et al.

(10) Patent No.: US 12,070,575 B2
(45) Date of Patent: Aug. 27, 2024

(54) CLINICAL-BASED AUTOMATED DELIVERY OF TREATMENT SUBSTANCES TO THE INNER EAR

(71) Applicant: Cochlear Limited, Macquarie University (AU)

(72) Inventors: John Michael Heasman, Hampton (AU); Jan Raymond Janssen, St. Ives (AU)

(73) Assignee: Cochlear Limited, Macquarie University (AU)

( * ) Notice: Subject to any disclaimer, the term of this patent is extended or adjusted under 35 U.S.C. 154(b) by 947 days.

(21) Appl. No.: 16/754,955

(22) PCT Filed: Oct. 4, 2018

(86) PCT No.: PCT/IB2018/057737
§ 371 (c)(1),
(2) Date: Apr. 9, 2020

(87) PCT Pub. No.: WO2019/073348
PCT Pub. Date: Apr. 18, 2019

(65) Prior Publication Data
US 2020/0238002 A1    Jul. 30, 2020

Related U.S. Application Data

(60) Provisional application No. 62/571,374, filed on Oct. 12, 2017.

(51) Int. Cl.
*A61M 5/142* (2006.01)
*A61M 5/172* (2006.01)
*A61N 1/05* (2006.01)

(52) U.S. Cl.
CPC ........ *A61M 5/14276* (2013.01); *A61M 5/172* (2013.01); *A61N 1/0541* (2013.01);
(Continued)

(58) Field of Classification Search
CPC .............. A61M 5/14276; A61M 5/172; A61M 2205/055; A61M 2205/3553;
(Continued)

(56) References Cited

U.S. PATENT DOCUMENTS 7,589,110 B2    9/2009   Puel
8,197,461 B1 *  6/2012   Arenberg .............. A61K 9/0046
                                                    604/500
(Continued)

FOREIGN PATENT DOCUMENTS

CN    102186528 A    9/2011
CN    107027288 A    8/2017
(Continued)

OTHER PUBLICATIONS

International Search Report and Written Opinion received in related International Application No. PCT/IB2018/057737, dated Apr. 24, 2019 (10 pages).
(Continued)

*Primary Examiner* — James D Ponton
(74) *Attorney, Agent, or Firm* — Edell, Shapiro & Finnan, LLC

(57) ABSTRACT

Presented herein are techniques for clinical-based automated control of the delivery of treatment substances to at least one inner ear of a recipient of an implantable medical device. More specifically, in-vivo biomarkers are analyzed to determine a biological state/status of one or more physiological elements of the inner ear. Subsequent delivery of one or more treatment substances to the inner ear of the recipient are controlled based on the determined biological state of the one or more physiological elements of the inner ear.

30 Claims, 7 Drawing Sheets

(52) U.S. Cl.
CPC .............. *A61M 2205/055* (2013.01); *A61M 2205/3553* (2013.01); *A61M 2205/3561* (2013.01); *A61M 2205/3569* (2013.01); *A61M 2205/3576* (2013.01); *A61M 2205/52* (2013.01); *A61M 2205/581* (2013.01); *A61M 2205/583* (2013.01); *A61M 2210/0662* (2013.01); *A61M 2230/08* (2013.01)

(58) Field of Classification Search
CPC .. A61M 2205/3561; A61M 2205/3569; A61M 2205/3576; A61M 2205/52; A61M 2205/581; A61M 2205/583; A61M 2210/0662; A61M 2230/08; A61M 5/14244; A61M 2039/0205; A61M 2205/50; A61M 39/0208; A61M 39/0247; A61M 39/04; A61N 1/0541
See application file for complete search history.

(56) References Cited

U.S. PATENT DOCUMENTS

| | | | |
|---|---|---|---|
| 9,072,468 B2 | 7/2015 | Buchman | |
| 2003/0097121 A1* | 5/2003 | Jolly | A61F 11/00 604/20 |
| 2006/0047318 A1 | 3/2006 | Pastore | |
| 2007/0213799 A1* | 9/2007 | Jolly | A61N 1/0541 607/137 |
| 2009/0209945 A1 | 8/2009 | Lobl et al. | |
| 2009/0259140 A1* | 10/2009 | Buchman | A61B 5/125 600/559 |
| 2010/0198281 A1 | 8/2010 | Chang | |
| 2011/0058485 A1* | 3/2011 | Sloan | G16H 40/67 370/242 |
| 2011/0288468 A1* | 11/2011 | Dadd | A61M 31/002 604/21 |
| 2012/0245534 A1* | 9/2012 | Jolly | A61N 1/0541 604/257 |
| 2012/0296176 A1* | 11/2012 | Herbst | A61B 5/4839 600/301 |
| 2014/0155811 A1* | 6/2014 | Gibson | A61N 1/32 604/20 |
| 2014/0221964 A1 | 8/2014 | Xiao et al. | |
| 2014/0275847 A1 | 9/2014 | Perryman et al. | |
| 2014/0350640 A1* | 11/2014 | Patrick | A61N 1/0541 607/57 |
| 2016/0246935 A1* | 8/2016 | Cerny | A61N 1/0551 |
| 2016/0354032 A1 | 12/2016 | Wariar | |
| 2017/0173262 A1 | 6/2017 | Veltz | |

FOREIGN PATENT DOCUMENTS

| | | |
|---|---|---|
| WO | 2009092067 A2 | 7/2009 |
| WO | 2015198167 A1 | 12/2015 |
| WO | 2016205272 A1 | 12/2016 |

OTHER PUBLICATIONS

Salt, A. N., & Plontke, S. K. R., "Local inner-ear drug delivery and pharmacokinetics," Drug Discovery Today, 10(19), 1299-1306, 2005, (14 pages).
Extended European Search Report in counterpart European Application No. EP18866767.9, mailed Jun. 4, 2021, 9 pages.
Extended European Search Report in counterpart European Application No. EP18866767.9, mailed Apr. 6, 2021, 9 pages.

* cited by examiner

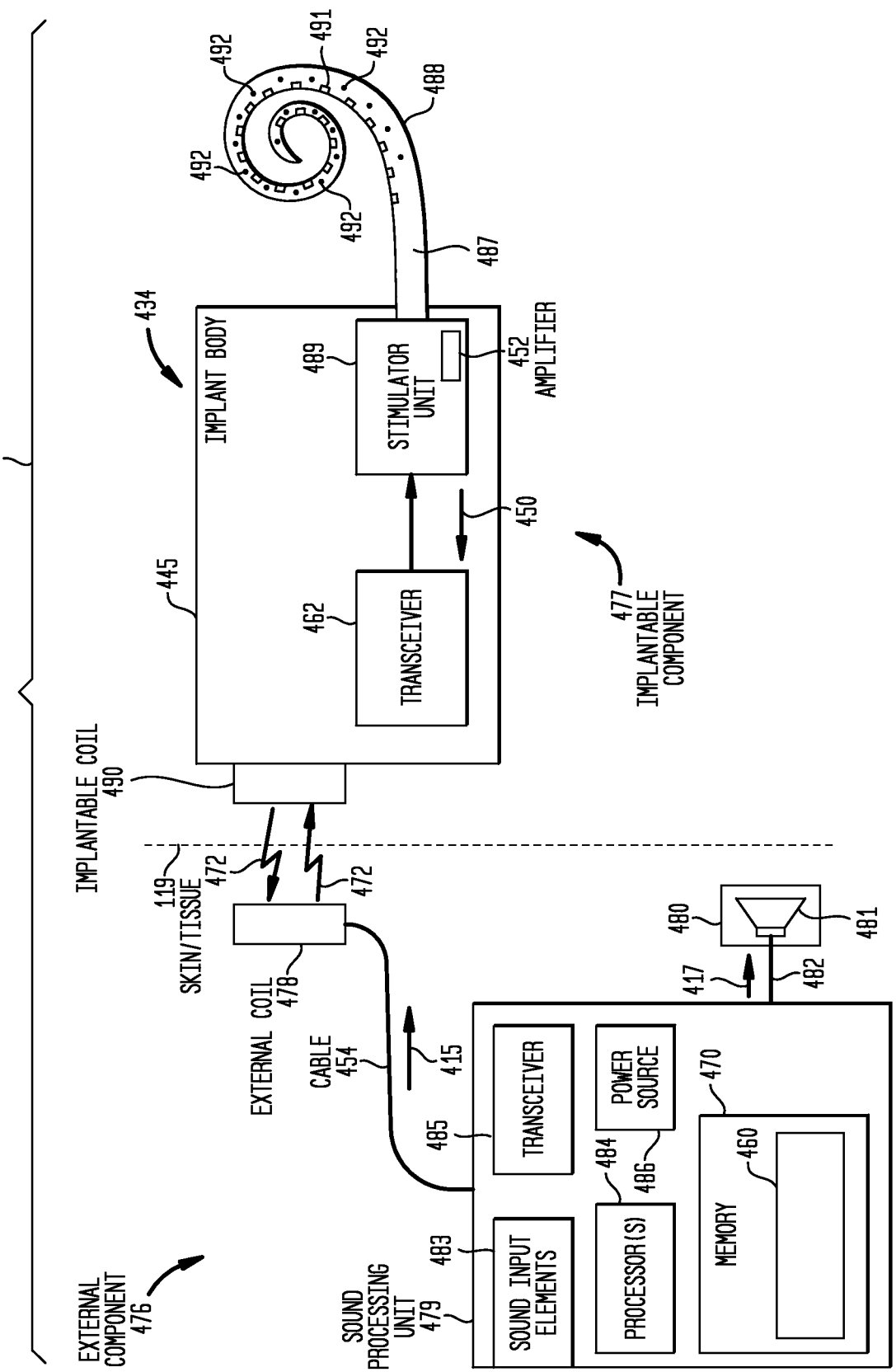

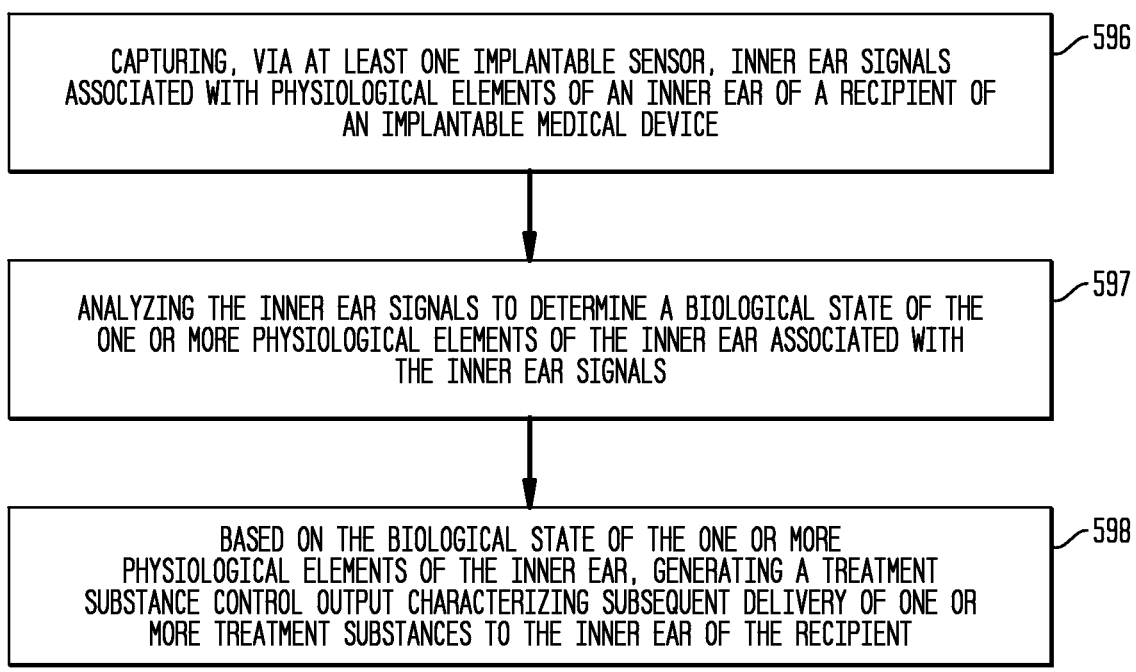

CLINICAL-BASED AUTOMATED DELIVERY OF TREATMENT SUBSTANCES TO THE INNER EAR

BACKGROUND

Field of the Invention

The present invention relates to clinical-based automated delivery of treatment substances to the inner ear of a recipient.

Related Art

A significant proportion of the world's population suffers from some form of inner ear disorder, such as conductive and/or sensorineural hearing loss, tinnitus, Meniere's disease or other balance disorders, etc. The primary treatments for inner ear disorders are based on auditory prostheses that mechanically and/or electrically stimulate the inner ear. For example, individuals suffering from conductive hearing loss, typically receive an auditory prosthesis that generates motion of the cochlea fluid. Such auditory prostheses include, for example, acoustic hearing aids, bone conduction devices, electro-acoustic devices, and direct acoustic stimulators. Individuals suffering from sensorineural hearing loss are unable to derive suitable benefit from auditory prostheses that generate mechanical motion of the cochlea fluid. As such, these individuals typically receive implantable auditory prostheses that stimulate nerve cells of the recipient's auditory system in other ways (e.g., electrical, optical and the like).

A growing area of research and development relates to the use of biological, bioactive, or other types substances, such as pharmaceutical agents, chemicals, nanoparticles, ions, drugs, etc. (generally and collectively referred to herein as "treatment substances"), to treat inner ear disorders alone, or in concert with an auditory prosthesis.

SUMMARY

In one aspect, a method is provided. The method comprises: capturing, via at least one implantable sensor, in-vivo biomarkers associated with physiological elements of an inner ear of a recipient of an implantable medical device; analyzing the in-vivo biomarkers to determine a biological state of the one or more physiological elements of the inner ear associated with the in-vivo biomarkers; and based on the biological state of the one or more corresponding physiological elements of the inner ear, generating a treatment substance control output characterizing subsequent delivery of one or more treatment substances to the inner ear of the recipient.

In another aspect, an implantable medical device system is provided. The implantable medical device system comprises: at least one sensor configured to be implanted in a recipient and configured to obtain one or more in-vivo biomarkers associated with the inner ear of the recipient; an implantable substance delivery component configured to control delivery of one or more treatment substances to the inner ear; and at least one processor configured to: analyze the one or more in-vivo biomarkers obtained from at least one sensor to determine at least one biological state of the inner ear; and based on the biological state of the inner ear, generate a substance delivery control signal defining control parameters for subsequent delivery of the one or more treatment substances to the inner ear by the implantable substance delivery component.

In yet another aspect, an implantable medical device is provided. The implantable medical device comprises: at least one sensor configured to be implanted in a recipient and configured to obtain one or more in-vivo biomarkers each associated with a physiological element of the inner ear of a recipient; an implantable substance delivery component configured to control delivery of one or more treatment substances to the inner ear; and at least one processor configured to analyze the one or more in-vivo biomarkers to generate automated control signals for regulation of delivery of the one or treatment substances to the inner ear of the recipient via the implantable substance delivery component.

BRIEF DESCRIPTION OF THE DRAWINGS

Embodiments of the present invention are described herein in conjunction with the accompanying drawings, in which:

FIG. 4B is a block diagram of the electro-acoustic hearing prosthesis of FIG. 4A; and FIG. 5 is a flowchart of a method, in accordance with certain embodiments presented herein.

DETAILED DESCRIPTION

Embodiments presented herein are generally directed to clinical-based automated administration/control (e.g., initiation, regulation, modification, etc.) of delivery of treatment substances to at least one inner ear of a recipient of an implantable medical device to treat an inner ear disorder (e.g., tinnitus, hearing loss, tinnitus, Ménière's disease, etc.). More specifically, in accordance with embodiments presented herein, in-vivo biomarkers are analyzed to determine a biological state/status of one or more physiological elements of the inner ear. Subsequent delivery of one or more treatment substances to the inner ear of the recipient are controlled based on the determined biological state of the one or more physiological elements of the inner ear. The use of the biological state of the one or more physiological elements ensures that that the subsequent delivery of the treatment substances remains in a desired treatment window (i.e., is clinically effective and does not have toxic effects).

Figure 1:
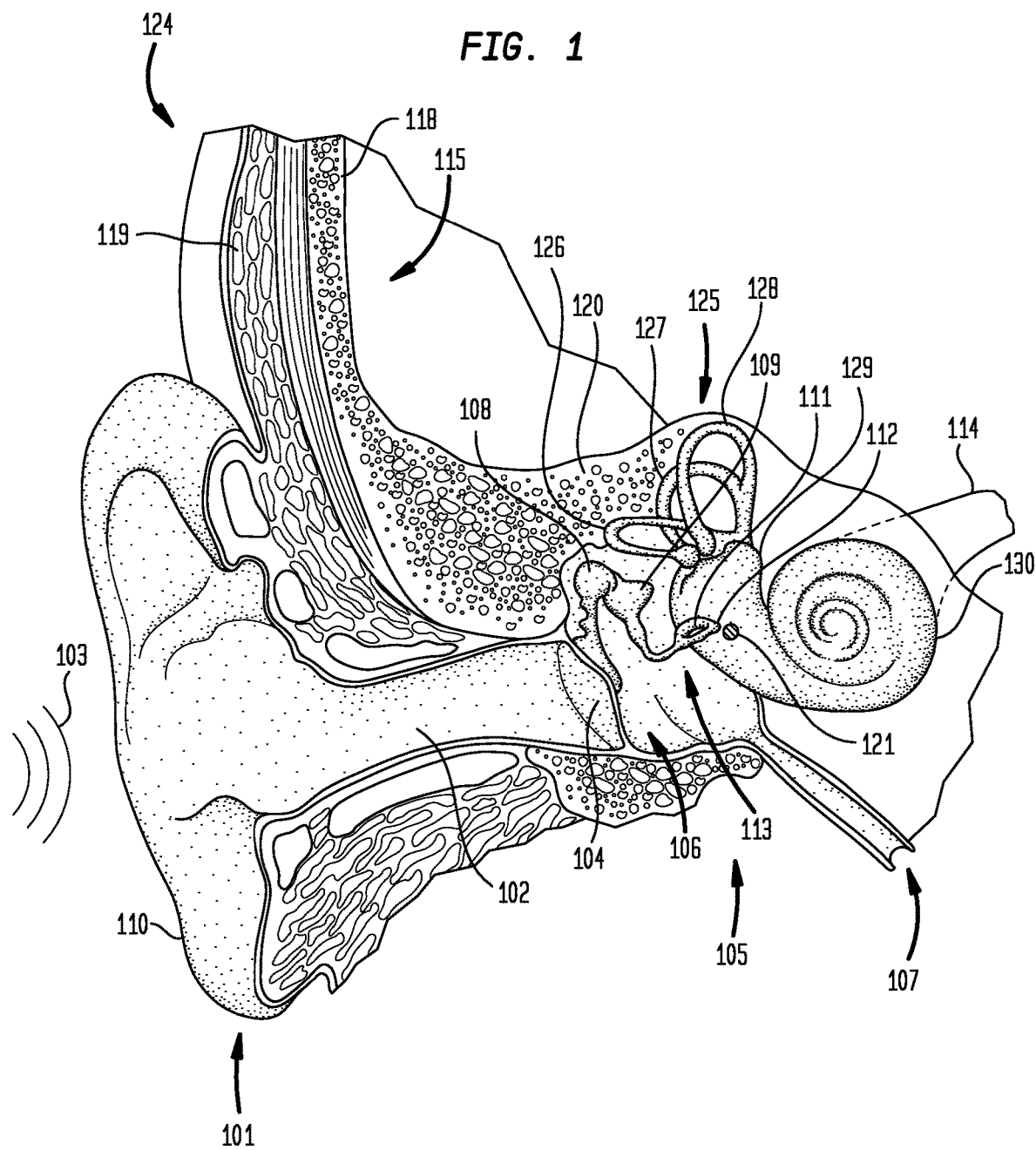
FIG. 1 is a schematic diagram illustrating the anatomy of a recipient at a location in which a delivery system herein may be implanted.

Before describing illustrative embodiments of the clinical-based automated treatment substance techniques presented herein, a brief description of the human anatomy of a recipient's ear is first provided with reference to FIG. 1.

More specifically, FIG. 1 illustrates that a recipient's ear comprises an outer ear 101, a middle ear 105, and an inner ear 107. In a fully functional ear, outer ear 101 comprises an auricle 110 and an ear canal 102. An acoustic pressure or sound wave 103 is collected by auricle 110 and channeled into and through ear canal 102. Disposed across the distal end of ear canal 102 is a tympanic membrane 104 which vibrates in response to sound wave 103. This vibration is coupled to oval window or fenestra ovalis 112, which is adjacent round window 121, through the bones of the middle ear 105. The bones of the middle ear 105 comprise the malleus 108, the incus 109 and the stapes 111, collectively referred to as the ossicles 106. The ossicles 106 are positioned in the middle ear cavity 113 and serve to filter and amplify the sound wave 103, causing oval window 112 to articulate (vibrate) in response to the vibration of tympanic membrane 104. This vibration of the oval window 112 sets up waves of fluid motion of the perilymph within cochlea 130. Such fluid motion, in turn, activates tiny hair cells (not shown) inside of cochlea 130. Activation of the hair cells causes appropriate nerve impulses to be generated and transferred through the spiral ganglion cells (not shown) and auditory nerve 114 to the brain (also not shown) where they are perceived as sound The human skull is formed from a number of different bones that support various anatomical features. Illustrated in FIG. 1 is the temporal bone 115 which is situated at the side and base of the recipient's skull 124 (covered by a portion of the recipient's skin/muscle/fat, collectively referred to herein as tissue 119). For ease of reference, the temporal bone 115 is referred to herein as having a superior portion 118 and a mastoid portion 120. The superior portion 118 comprises the section of the temporal bone 115 that extends superior to the auricle 110. That is, the superior portion 118 is the section of the temporal bone 115 that forms the side surface of the skull. The mastoid portion 120, referred to herein simply as the mastoid 120, is positioned inferior to the superior portion 118. The mastoid 120 is the section of the temporal bone 115 that surrounds the middle ear 105.

Also shown in FIG. 1 are the semicircular canals 125, which are three half-circular, interconnected tubes located adjacent to the cochlea 130. The three canals are the horizontal semicircular canal 126, the posterior semicircular canal 127, and the superior semicircular canal 128. The canals 126, 127 and 128 are aligned approximately orthogonally to one another. Specifically, when the individual's head is in an upright position, the horizontal canal 126 is aligned roughly horizontally in the head, while the superior canal 128 and the posterior canal 127 are each aligned roughly at a 45 degree angle to a vertical through the center of the individual's head.

Each canal 126, 127, and 128 is filled with a fluid called endolymph and contains a motion sensor with tiny hairs (not shown) whose ends are embedded in a gelatinous structure called the cupula (also not shown). As the orientation of the skull changes, the endolymph is forced into different sections of the canals. The hairs detect when the endolymph passes thereby, and a signal is then sent to the brain. Using these hair cells, horizontal canal 126 detects horizontal head movements, while the superior 128 and posterior 127 canals detect vertical head movements. Vestibule 129 provides fluid communication between the semicircular canals 125 and the cochlea 130.

As noted, it may be advantageous to deliver treatment substances to inner ear 107, including the cochlea 130 and the vestibular system (i.e., the semicircular canals 125, vestibule 129, the utricle, and the saccule), to treat a number of inner ear disorders (e.g., tinnitus, hearing loss, tinnitus, Ménière's disease, etc.). However, there are a number of challenges, particular with respect to achieving consistent and beneficial clinical/treatment effect (e.g., crude titration estimation based, for example, on normative statistics, inability to monitor clinical efficacy, etc.), that have limited the use of treatment substances for inner ear disorders. These challenges relate to variability associated with where the treatment substances reach within the inner ear, delivery techniques, time course, anatomical and biological variability, etc. As described further below, presented herein are techniques for clinical-based automation of the delivery of treatment substances to the inner ear of a recipient of an implantable medical device, such as a recipient of implantable treatment substance delivery systems, implantable hearing/auditory prostheses, etc. The clinical-based automation is based on an electrically measured biological state of one or more physiological elements of the inner ear and is configured to ensure that delivery of the treatment substances remains in a selected/desired treatment window (i.e., is clinically effective and does not have toxic effects). The use of the biological state of one or more physiological elements to automate the treatment substance delivery may address some of the challenges associated with conventional treatment substance delivery techniques.

The clinical-based automated treatment substance delivery techniques presented herein may be implemented by a number of different types of implantable medical devices. Merely for ease of illustration, the clinical-based automated treatment substance delivery techniques will be primarily described herein with reference to stand-alone treatment substance delivery systems. However, as described elsewhere herein, it is to be appreciated that a number of different other implantable medical devices, including implantable hearing prostheses (e.g., cochlear implants, electro-acoustic prostheses, direct acoustic stimulators, etc.), can be configured to implement the treatment substance delivery techniques presented herein. That is, a treatment substance delivery system may be incorporated into other implantable medical devices that perform one or more additional therapeutic/treatment functions (i.e., functions other than delivery of treatment substances).

Figure 2A:
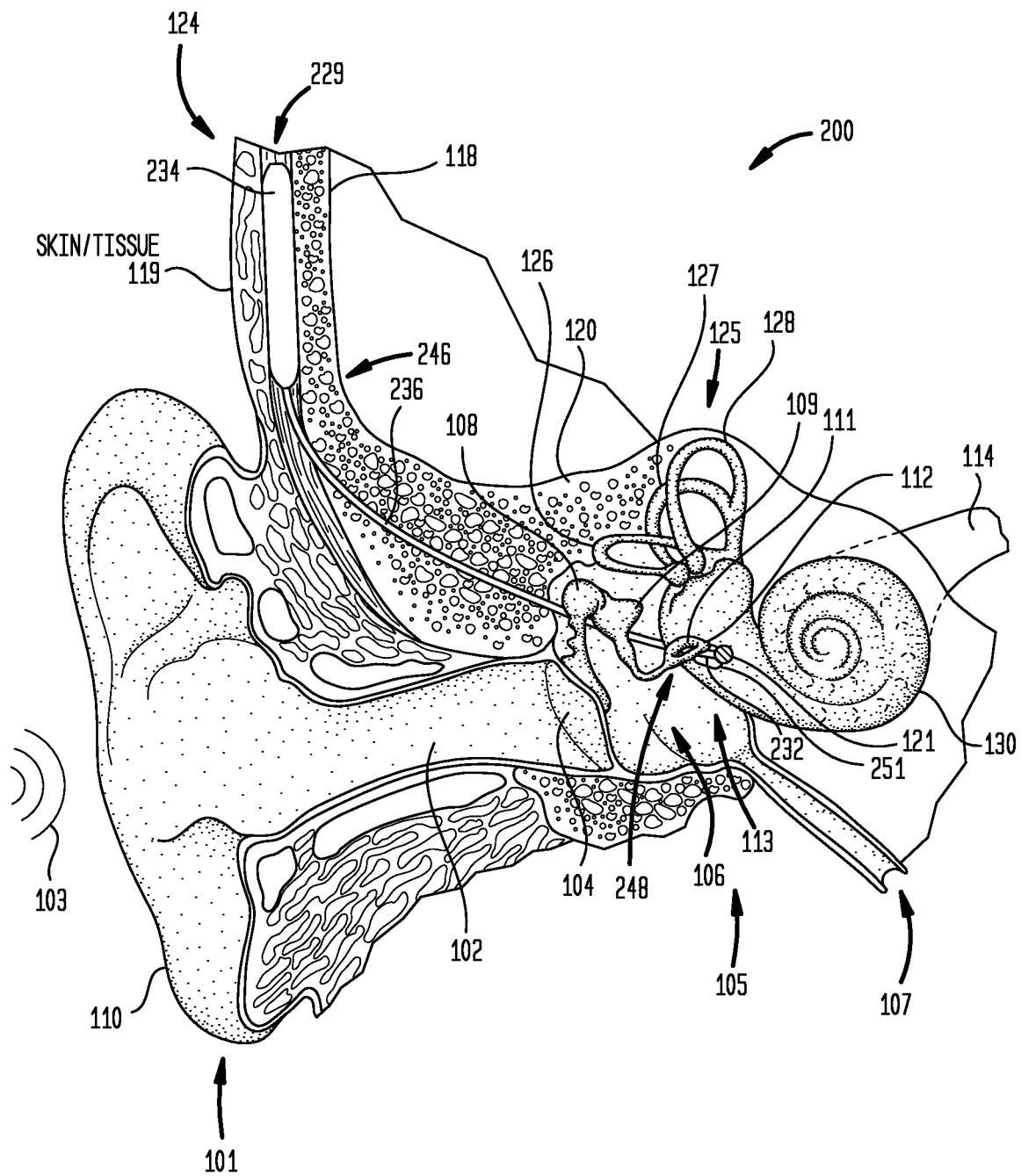
FIG. 2A illustrates a clinical-based automated substance delivery system in accordance with certain embodiments presented herein implanted in a recipient.
Figure 2B:
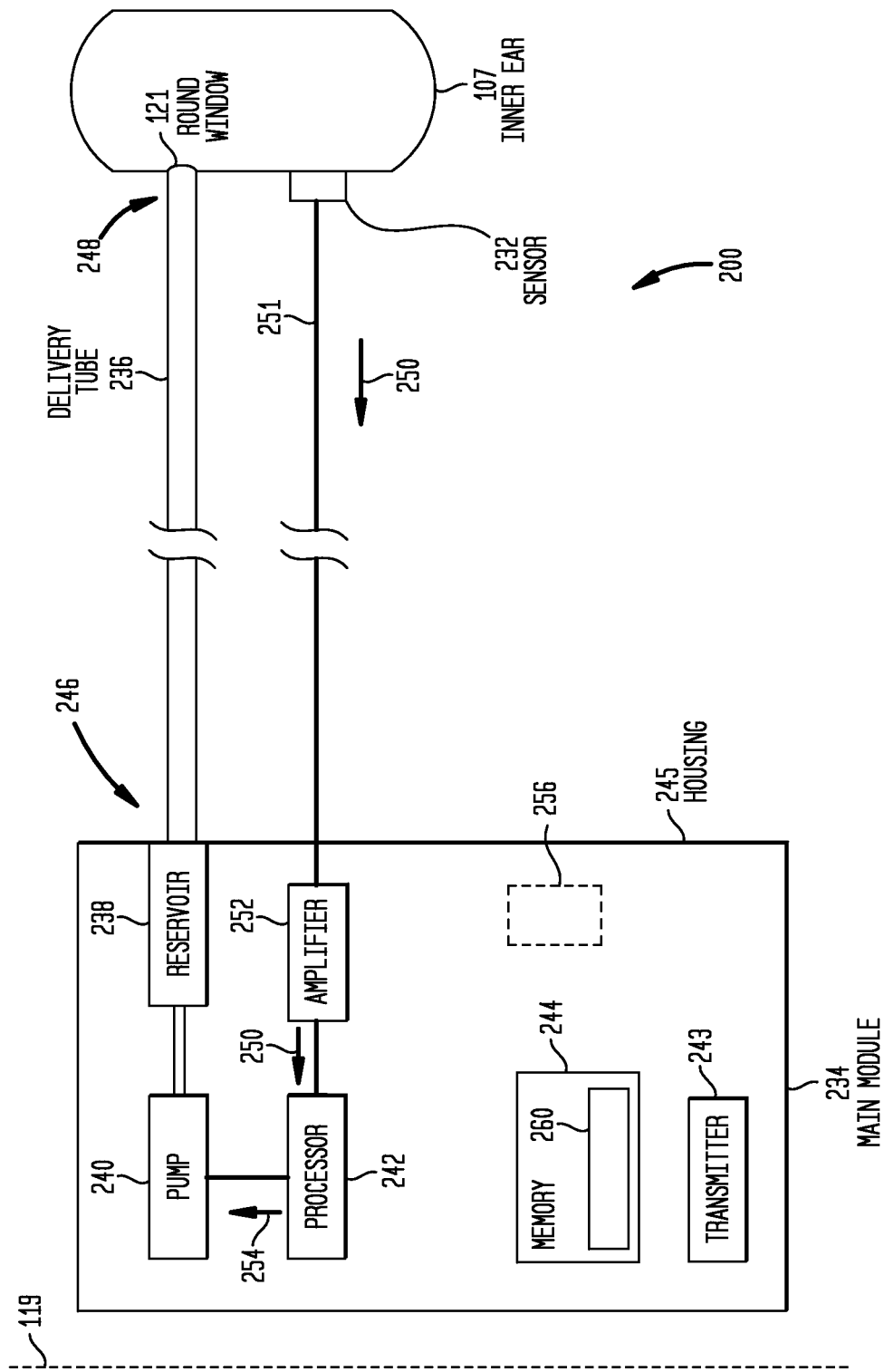
FIG. 2B illustrates a first portion of the clinical-based automated substance delivery system of FIG. 2A.

FIG. 2A is a schematic diagram illustrating an implantable treatment substance delivery system (substance delivery system) 200 in accordance with embodiments presented herein, while FIG. 2B is a block diagram of the substance delivery system 200. For ease of description, FIGS. 2A and 2B will generally be described together. Also for ease of description, in FIG. 2A the substance delivery system 200 is shown implanted in the human anatomy of FIG. 1.

The substance delivery system 200 is, in general, configured to deliver treatment substances to inner ear 107 and comprises, among other elements, one or more implantable sensors 232, an implant body (main module) 234, and a delivery tube 236. As shown in FIG. 2B, the main module 234 comprises, among other elements, a reservoir 238, a substance delivery pump 240, at least one processor 242, a transmitter 243, and a memory 244, all of which are disposed within a housing 245.

In the embodiment of FIGS. 2A-2B, the main module 234 is positioned within the recipient underneath a portion of the recipient's tissue 119. The main module 234 may be positioned between layers of the recipient's tissue 119 or may be adjacent to a subcutaneous outer surface 229 of the recipient's skull. For example, the main module 234 may be positioned in a surgically created pocket at the outer surface 229 (i.e., adjacent to a superior portion 118 of the temporal bone 115).

As noted, in this example the main module 234 comprises at least one reservoir 238. Prior to or after implantation, the reservoir 238 is at least partially filled with a treatment substance for delivery to the inner ear 107 of the recipient.

The treatment substance may be, for example, in a liquid form, a gel form, comprise nanoparticles or pellets, etc., and is designed to "treat" (e.g., remediate, rehabilitate, etc.) and inner ear disorder, such as tinnitus, hearing loss, tinnitus, Meniere's disease, etc. In certain arrangements, the treatment substance may initially be in a crystalline/solid form that is subsequently dissolved. For example, reservoir 238 could include two chambers, one that comprises a fluid (e.g., artificial perilymph or saline) and one that comprises the crystalline/solid treatment substance. The fluid may be mixed with the crystalline/solid treatment substance to form a fluid or gel treatment substance that may be subsequently delivered to the recipient.

In certain embodiments, the reservoir 238 includes a needle port (not shown) that enables the reservoir 238 to be refilled via a needle injection through the tissue 119. In other embodiments, the reservoir 238 may be explanted and replaced with another reservoir that is, prior to or after implantation, at least partially filled with a treatment substance. The delivery tube 236 includes a proximal end 246 and a distal end 248. The proximal end 246 of the delivery tube 236 is fluidically coupled to the reservoir 238, while the distal end 248 of the delivery tube 236 is fluidically coupled to the recipient's inner ear 107. In this example, the distal end 248 is fluidically coupled to the round window 121. The delivery tube 236 may be secured within the recipient so that the distal end 238 remains located adjacent to the round window 121.

The pump 240 may be, for example, an osmotic pump, infusion pump, or other substance delivery component/device that is activated (by the processor 242) to release a treatment substance from the reservoir 238 into the proximal end 246 of the delivery tube 236. Once released, the treatment substance travels to the distal end 248 of the delivery tube 236 for application to the inner ear 107 (e.g., the round window 121).

In accordance with embodiments presented herein, the processor 242 is configured to administer/control (e.g., initiate, regulate, modify, etc.) delivery of treatment substances to the inner ear 107 based on a "biological status" or "biological state" of one or more physiological elements of the inner ear. The one or more physiological elements of the inner ear 107 may comprise, for example, sensory cells in the inner ear (e.g., hair cells), neural elements (e.g., synapses and neural bodies), immunoresponsive cells (e.g., macrophages), and/or other supporting cells or structures of the inner ear 107. The biological status/state of a physiological element of the inner ear may include, for example, the homeostasis of the inner ear, the inner ear health (e.g., inflammation or apotosis), biophysical function, location and density of the physiological element, etc., and may be used to quantify or assess the clinical/treatment effect, in terms of pharmokinetics, concentration, toxicity, and/or efficacy, of a prior delivery of one or more treatment substances to the inner ear.

The biological state of the one or more physiological elements of the inner ear 107 is evaluated by the processor 242 based on "in-vivo biomarkers" or, more simply, "biomarkers" that are obtained from the one or more implantable sensors 232 associated with the inner ear 107.

In certain embodiments, the in-vivo biomarkers are measurable electric potentials from either the inner ear or from higher order neural processing. These potentials may include, for example, electrophysiological potentials, neurological potentials, higher-order potentials, and electrode voltages, all of which are obtained from the inner ear itself or related anatomical structures nearby and which reflect the biological state of one or more corresponding/associated physiological elements of the inner ear. In other embodiments, the in-vivo biomarkers are signals that are not necessarily obtained from the inner ear, but reflect the biological state of one or more corresponding/associated physiological elements of the inner ear (e.g., accelerometer signals in the case of vestibular dysfunction).

The in-vivo biomarkers are obtained through one or more in-situ electrical measurements, such as: (1) electrode voltage measurements, (2) electrophysiological measurements (e.g., electrocochleography (ECoG) measurements, electrically evoked compound action potential (ECAP) measurements, higher evoked potential measurements from the brainstem and auditory cortex, measurements relating to neural and mechanoreceptors, these being the hair cells in the cochlea and vestibular system), (3) biological measurements (e.g., biosensors), and (4) external measurements (e.g., accelerometers).

An ECAP measurement refers to the capture of a set of electrical potentials generated in the recipient's cochlea 130 in response to the delivery of electrical stimulation to the cochlea. In contrast, an ECoG measurement refers to the capture of a set of electrical potentials generated in the recipient's cochlea 130 (e.g., in response to the delivery of acoustic stimulation to the cochlea, measurement of background activity that is not linked to a specific input, but rather to the spontaneous nature of the inner ear either in the absence or presence of input, etc.). The captured electrical potentials (i.e., a set of ECoG responses) may include a plurality of different stimulus related electrical potentials, such as the cochlear microphonic (CM), the cochlear summating potential (SP), the auditory nerve neurophonic (ANN), and the auditory nerve Action Potential (AP), which are measured independently or in various combinations. The cochlear microphonic is an alternating current (AC) voltage that mirrors the waveform of the acoustic stimulus at both low, moderate and high levels of acoustic stimulation. The cochlear microphonic is generated by the outer hair cells of the organ of Corti and is dependent on the proximity of the recording electrode(s) to the stimulated hair cells and the basilar membrane. In general, the cochlear microphonic is proportional to the displacement of the basilar membrane by the travelling wave phenomena.

The summating potential is the direct current (DC) response of the outer hair cells of the organ of Corti as they move in conjunction with the basilar membrane (i.e., reflects the time-displacement pattern of the cochlear partition in response to the stimulus envelope). The summating potential is the stimulus-related potential of the cochlea and can be seen as a DC (unidirectional) shift in the cochlear microphonic baseline. The direction of this shift (i.e., positive or negative) is dependent on a complex interaction between stimulus parameters and the location of the recording electrode(s).

The auditory nerve neurophonic is a signal recorded from the auditory nerve, while the auditory nerve Action Potential represents the summed response of the synchronous firing of the nerve fibers in response to the acoustic stimuli, and it appears as an alternating current voltage. The auditory nerve Action Potential is characterized by a series of brief, predominantly negative peaks, including a first negative peak (N1) and second negative peak (N2). The auditory nerve Action Potential also includes a magnitude and a latency. The magnitude of the auditory nerve Action Potential reflects the number of fibers that are firing, while the latency of the auditory nerve Action Potential is measured as the time between the onset and the first negative peak (N1).

Certain in-situ electrical measurements rely upon the delivery of stimulation to the inner ear 107. In certain examples, the substance delivery system 200 may be configured to deliver test/measurement stimulation (i.e., acoustic, electrical, or other types of signals configured to evoke a measurable response). For example, as described further below, the implantable sensor 232 may be an electrode that can be used to capture in-vivo biomarkers. In such embodiments, the electrode 232 may also be configured to deliver measurement stimulation to the inner ear 107 (i.e., deliver stimulation that induces a response), as well as to capture the resulting response. In other embodiments, the substance delivery system 200 may operate with another external or implantable device that is capable of either delivering acoustic, electrical, or other types of stimulation signals to the inner ear 107 (e.g., via air conduction, bone conduction, direct acoustic stimulation of the inner ear, etc.). For example, a receiver (not shown in FIG. 2A or 2B) could be positioned at the outer ear 101 or the ear canal 102 to acoustically stimulate the inner ear 107.

As noted above, certain embodiments of the present invention may be implemented in systems that may not be configured to deliver acoustic, electrical, or other types of stimulation to a recipient (e.g., systems that do not have sound processing capabilities, such as a dedicated drug delivery system). In such embodiments, as described further below, the in-vivo biomarkers could be obtained in response to environmental (e.g., unaided) sounds.

Biological measurements refer to measurements that capture information related to the state of the biological environment of the inner ear, including the homeostasis of the inner ear, the presence and concentration of biological cell types such as macrophages and proteins, etc., as detected by a biosensor. The biosensor provides an electrical output representing the state of the biological environment for further analysis. The homeostasis of the inner ear refers to the constant equilibrium of the chemical environment in the inner ear. Maintenance of the homeostasis is critical to ensure the cells related to hearing function are protected and maintained. Examples of the types of biological biomarkers from biosensors may include, for example, the level of potassium and sodium levels in the perilymph within the cochlea 130 and/or other chemical and biochemical measures (e.g., to ascertain if homeostasis has been compromised or has altered since implantation of the cochlear implant).

In summary, in accordance with examples presented herein, the at least one sensor 232 is used to perform one or more in-situ electrical measurements. The in-situ electrical measurements, which may be activated/triggered by the processor 242, in response to environmental sounds, etc., result in the capture of one or more in-vivo biomarkers which represent the biological state of one or more corresponding/associated physiological elements of the inner ear. The captured in-vivo biomarkers are generally represented in FIG. 2B by arrow 250.

An implantable sensor in accordance with embodiments presented herein is equipped or interfaced with a biological amplifier that is configured to capture the one or more in-vivo biomarkers from the sensor. In the specific example of FIGS. 2A and 2B, the one or more implantable sensors 232 include an electrode that is disposed on or near the round window 121. It is to be appreciated that the location for electrode 232 shown in FIGS. 2A and 2B is illustrative and that the electrode 232 may be disposed at other anatomical locations including, but not limited to, within the cochlea 130 or semicircular canals 125, the tympanic membrane, other extra-cochlear locations, etc.

The electrode 232 interfaces with a biological amplifier 252 via, for example, a wire/lead 251. In other words, the biological amplifier 252 is configured to measure the electrical potentials detected at the electrode 232 via wire 251 (e.g., measure a fixed duration measurement window of sampled electrical potentials from the electrode 232 or monitor a voltage waveform detected at the electrode 232), where the potentials originate from, for example, biological structures such as nerves, muscle, and hair cells etc. For electrophysiological signals, the detected signals are generally small in nature, thus the biological amplifier 252 is configured to amplify the detected signals to ensure their detection above the noise of the system. That is, the biological amplifier 252 is configured to generate amplified version of the in-vivo biomarkers and to send the amplified in-vivo biomarkers 250 to the processor 242. For ease of description, the amplified version of the in-vivo biomarkers are referred to herein simply as in-vivo biomarkers 250.

As noted, the in-vivo biomarkers 250 represent a biological state of one or more corresponding/associated physiological elements of the inner ear. For example, the in-vivo biomarkers 250 may represent a biological state for one or more of: sensory hair cells, afferent/efferent nerve fibers, synapses, supporting cells, vestibular function/cells, immunological response/pathways (including fibrosis), etc. The processor 242 is configured to analyze the in-vivo biomarkers 250 to determine a biological state of the one or more corresponding physiological elements of the inner ear (i.e., the physiological elements relating to the captured in-vivo biomarkers). In certain embodiments, the biological state of the one or more corresponding physiological elements is used to quantify or assess a clinical effect, in terms of pharmokinetics, concentration, toxicity, and/or efficacy, of a prior delivery of a treatment substance to the inner ear 107. Based on the biological state of the one or more physiological elements of the inner ear (as determined by the processor 242), and possibly the quantification or assessment of the clinical effect, the processor 242 is configured to generate a "treatment substance control output" relating to the subsequent delivery of the treatment substance within reservoir 238 to the inner ear 107. The use of the biological state of the one or more physiological elements ensures that that the subsequent delivery of the treatment substances remains in a desired treatment window (i.e., is clinically effective and does not have toxic effects).

In general, the analysis performed by the processor 242 may take a number of different forms and may depend on, for example, the in-vivo biomarkers 250 that are obtained/captured. In certain embodiments, the analysis performed by the processor 242 can include, but is not be limited to, a comparison of the determined biological state of one or more physiological elements (as determined from the captured in-vivo biomarkers) against one or more predetermined biological states. More specifically, the determined biological state of one or more physiological elements could be compared against: a baseline measure which represents the biological state of the same one or more physiological elements of the recipient's inner ear 107 prior to delivery of a treatment substance to the inner ear (e.g., determined based on prior in-vivo biomarkers), a biological state determined based on normative data (e.g., from a normative sample of the recipient population), or other type of comparison. In such embodiments, the comparison may be absolute, frequency-based, template/pattern based (i.e., an amplitude or frequency domain operation in which the measured signals are correlated with a known template/pattern that was, for example, previously observed for the recipient, determined from normative data, etc.), or other type of comparison. In certain embodiments, the baseline measure may also comprise measures made prior to the insertion of elements (e.g., electrode array, treatment delivery device, etc.) into the inner ear 107 to account for changes relating to the surgery itself. It is also to be appreciated that two or more different sets of in-vivo biomarkers may be combined or compared with each other to provide additional information for use by the processor 242.

In one embodiment, the processor 242 is configured to analyze spectral aspects of captured in-vivo biomarkers 250. For example, the processor 242 may be configured to analyze the in-vivo biomarkers 250 for changes to the power spectral density of the waveform under analysis. This analysis may include analysis of peaks, tilts, shifts in the frequency spectrum, or other spectral information (e.g., information indicating some change in the measured signals from a baseline measurement). In the same or other embodiments, a biosensor is employed to either determine either biochemical composition or biological content. In the case of determining biochemical composition, the sensor would provide information on specific target molecules or substances using methods such as spectral fingerprint, concentration levels and/or mass of the molecules. These measures would then be used to determine the pharmodynamics, pharmokinetics or presence of unwanted bi-products (or toxic effects) each of which that can be used as an input to the controller of the substance delivery.

In the same or other embodiments, the processor 242 is configured to analyze the amplitudes of in-vivo biomarkers 250 in comparison to basement measurements. For example, the processor 242 may analyze amplitude changes via application of a statistical measure, such as a median or Root mean square (RMS) measure, to quantify signal amplitude differences observed over time.

The processor 242 may also or alternatively be configured to monitor (e.g., constantly) in-vivo biomarkers 250 or other in-vivo bio-markers over a time period in to detect/identify changes that may require action by the controller. Detected changes may be compared to a known reference state (baseline) measure (e.g., a biological state in the recipient at an earlier point in time, a prescribed target based on individual factors of the recipient, normative data, etc.).

In one example, in-vivo biomarkers 250 are analyzed by the processor 242 for evaluation of a recipient's tinnitus. For example, the in-vivo markers 250 monitored for changes (e.g., an increase) in spontaneous neural activity in the absence of stimulation that could indicate the presence of, or changes in, the recipient's tinnitus (e.g., an increase in spontaneous neural activity in the absence of stimulation could indicate the recipient's tinnitus is getting worse). As described further below, the analysis of the in-vivo biomarkers 250 in relation to the presence of, or changes in, the recipient's tinnitus may be used to generate a treatment substance control output that, accordingly, controls the delivery of a treatment substance to the inner ear that is operable to treat the tinnitus.

In another example, in-vivo biomarkers 250 are analyzed by the processor 242 for ototoxic effects of treatments for Meniere's disease. In these examples, the outer and inner hair cells are monitored (based on corresponding in-vivo biomarkers 250) to flag changes in either the relative amplitude, pattern over time or relative morphology. Electrical measurements can also be made to obtain in-vivo biomarkers 250 from the vestibular system to quantify or assess substance clinical effects and vestibular function.

In another example, in-vivo biomarkers 250 are analyzed by the processor 242 to determine spiral ganglion nerve (SGN) density estimates during the administration of brain-derived neurotrophic factors (BDNF). Here, the neural response of the ECOG and ECAP is monitored to provide estimates of changes in SGN survival at various locations in the cochlea. Certain such examples may be implemented with an intra-cochlear stimulating, such as that described below with reference to FIGS. 4A and 4B, to obtain in-vivo biomarkers from different points within the cochlea.

In another example, in-vivo biomarkers 250 are analyzed by the processor 242 to determine detect hair cell and synaptic changes during the administration of treatment substances with protective benefits, such as growth factors. Relative changes to the cochlea microphonic (CM) could be monitored (e.g., via either intra- or extra-cochlear electrodes) to assess the relative population changes in the outer hair cells within the cochlea in response to the substance delivery system.

As noted above, in certain embodiments, the in-vivo biomarkers 250 are captured as part of an ECoG measurement (i.e., the capture of a set of electrical potentials generated in the recipient's cochlea 130 in response to acoustic stimulation, unaided environmental sounds, background activity that is not linked to a specific input, but rather to the spontaneous nature of the inner ear either in the absence or presence of input, etc.). That is, certain recipients may have sufficient residual hearing such that unaided environmental sounds are sufficient to evoke an ECOG response (i.e., measureable electrical potentials). However, for certain hearing impaired recipients, unaided environmental sounds may be insufficient to evoke measurable response and, as such, aided acoustic inputs would be utilized. The acoustic inputs could be delivered in a number of different manners such as, for example, a receiver in the drug delivery system and/or in a separate hearing aid, an implanted bone conduction device, an external bone conduction device (e.g., a headband device, a device that can be clipped onto the teeth), etc.

For individuals with a hearing impairment, a microphone or accelerometer integrated in the delivery system 200 or in a separate component (e.g., a hearing aid), a wireless microphone, or other element could be used to determine the acoustic environment and correlate and/or trigger the ECoG measurement. An accelerometer could also be used to, for example, only trigger recordings when the user's own voice was present and to record and determine when the signal was at an appropriate level.

In certain embodiments, the in-vivo biomarkers could be derived from aggregate ECoG measures taken during a sample period that's sufficiently long to assume broad spectrum sound exposure (e.g., without the need for hardware such as microphone, accelerometer, etc.). In certain such embodiments, during the implantation of the delivery system, a baseline activity of the cochlea, including ECoG evoked using multiple frequencies or complex inputs, could be measured. This baseline (and signal input) would be representative of a long term expected average that should be measured during activities of daily living. The processor 242 could then compare subsequent bio-markers (e.g., captured in response to unaided environment sounds) against the baseline, for example, on a periodic basis (greater than one day) to determine relative changes to the acquired signal that would be indicative to changes to the cochlea health Returning to the example of FIGS. 2A and 2B, as noted the processor 242 analyzes in-vivo biomarkers 250 to generate an appropriate treatment substance control output which ensures that delivery of the treatment substances remains in a desired treatment window. In general, the treatment substance control output may have a number of different forms. For example, in the embodiment of FIGS. 2A and 2B, the treatment substance control output comprises one or more "substance delivery control signals," represented in FIG. 2B by arrow 254, that are provided to the pump 240 so as to control/regulate (e.g., initiate, adjust, etc.) delivery of the treatment substance within reservoir 238 to the inner ear 107. The substance delivery control signals 254 may represent or define, for example, the concentration, dose, or other control parameters for the subsequent delivery of the treatment substance to the inner ear 107 of the recipient. In certain embodiments, the substance delivery control signals 254 are generated based on a quantification or assessment of the clinical effect, in terms of pharmokinetics, concentration, toxicity, and/or efficacy, of a prior delivery of a treatment substance to the inner ear 107 (i.e., the control parameters for the subsequent delivery of the treatment substance are based on the clinical effect of the prior delivery of a treatment substance to the inner ear 107).

Using the substance delivery control signals 254, operation of the pump 240 can be automatically set so that the subsequent delivery of the treatment substance to the inner ear 107 complies with the parameters set by the processor 242. Stated differently, the substance delivery control signals 254 generated by the processor 242 are a form of closed-loop feedback that is used to auto-regulate the delivery of the treatment substance to the inner ear 107 (i.e., trigger a change in the controller of the pump 240 to, for example, increase or decrease dosage, concentration, etc. of the treatment substance delivered to the inner ear based on the biological state of the one or more physiological elements of the inner ear).

As noted, the generation of substance delivery control signals 254 are an example of the treatment substance control output(s) that can be generated by the processor 242. It is to be appreciated that the processor 242 may also or alternatively generate other types of treatment substance control output(s). For example, in the same or other embodiments, the treatment substance control output(s) generated by the processor 242 may comprise a signal that initiates the sending of a wireless notification to an external device for generation of an audible or visible notification to the recipient, a clinician, caregiver, or other user. The notification may indicate, for example, recommended changes to the dose or dosage of the treatment substance (e.g., modify dosage systemically such as through oral consumption, concentration, etc. Therefore, in certain embodiments, the processor 242 initiates, via a wireless transmitter 243, the sending of information to a user to relating to changes in the treatment substance delivery. The external device may be, for example, a mobile device (e.g., mobile phone), computer, etc.

As noted, FIGS. 2A and 2B illustrate an embodiment in which the one or more implantable sensors include a single electrode 232. It is to be appreciated that the use of a single electrode is merely illustrative and that a number of other implantable sensors may be used in alternative embodiments either alone or in various combinations.

For example, in certain embodiments multiple electrodes may be used as the implantable sensors that provide in-vivo biomarkers to the processor 242. In embodiments that include one or more electrodes, one or multiple electrodes may be used to capture in-vivo biomarkers, such as in response to the delivery of charge to the same or other (e.g., neighboring) electrode. These embodiments may include techniques such as impedance spectroscopy and/or may include the ability to apply phased array stimulation and multi-electrode recordings. As noted, in certain embodiments, electrical measurement of the electrode voltages provide information on the biological state of one or more physiological elements of the inner ear which, in turn, provide information on inflammatory processes, immune response changes, biological environment changes and homeostasis of the cochlea and vestibular system, etc.

In other embodiments, the one or more implantable sensors can include an accelerometer, which is a physical device configured to capture rate of change of velocity either in one or more dimensions (e.g., a three-dimensional accelerometer). In these embodiments, the changes in the long-term behavior of the accelerometer output signals, which are in-vivo biomarkers provided to the processor, can be employed to monitor, for example, the balance of the individual to quantify or assess the efficacy of the treatment or side-effects, such as balance problems. In certain such embodiments, the accelerometer may be built into the main module 234 or other component of the delivery system 200. The possible inclusion of an accelerometer 256 is shown in FIG. 2B using dashed lines.

In further embodiments, the one or more implantable sensors can include a biosensor, such as an optical biosensor, an electrochemical biosensor, a mass biosensor, etc., configured to provide an electrical output representing a biological state of the inner ear 107. An optical biosensor is a device that employs the use of light to extract data from physical properties of a target object, such as changes to the reflective index of a metal. An electrochemical biosensor is a device that employs one or more of potentiometry, amperometry, and conductometry to analyze the content of a biological sample. In accordance with embodiments presented herein, an optical biosensor or an electrochemical biosensor may be used to detect the presence or concentration of target molecules based on their spectral fingerprint. Such information may enable the processor 242 to assess the biological environment, presence of target molecules, pharmokinetics and pharmodynamics, etc. Certain biosensors may also be capable of monitoring the concentration levels of the substance being delivered to account for clearance rates in the cochlea, for example.

A mass biosensor is a device that uses surface acoustic waves and piezoelectric effects for biosensing various parameters, such as metabolites, proteins, antigens, and microorganisms, etc. In accordance with embodiments presented herein, a mass biosensor may be used to quantify and detect changes to the inner ear biological environment and/or the presence and concentration of the treatment substances in use.

In certain examples, biosensors may be used with a microfluidics system that is configured to precisely control fluids (e.g., at a sub-millimeter scale) to enable fluid movement, mixing, separation, etc. for eventual analysis by the biosensors. For example, with a microfluidics system can provide the a mechanism for on-going sampling small quantities of fluid, such as blood, perilymph, cerebrospinal fluid (CSF), etc. to quantify or assess biological state and drug pharmokinetics and pharmodynamics FIGS. 2A and 2B illustrate an arrangement in which the substance delivery system 200 includes an on-board controller (i.e., processor 242) that is configured to provide clinical-based automated (closed-loop) control of the delivery of treatment substances to the inner ear 107 (i.e., clinical-based automated control of the substance delivery components, namely pump 240). In the embodiment shown in FIG. 2B, the processor 242 is configured to execute software, namely inner ear analysis logic 260 stored in memory 244, to analyze the in-vivo biomarkers and generate the treatment substance control output(s), as described above.

As shown in FIG. 2B, the memory 244 may be read only memory (ROM), random access memory (RAM), or another type of physical/tangible memory storage device. Thus, in general, the memory 244 may comprise one or more tangible (non-transitory) computer readable storage media (e.g., a memory device) encoded with software comprising computer executable instructions and when the software is executed (by the processor 242) it is operable to perform the operations described herein to analyze the in-vivo biomarkers and generate the treatment substance control output(s).

FIGS. 2A and 2B illustrate an embodiment in which the treatment substance is delivered at/via the round window 121. It is to be appreciated that the treatment substances could also or alternatively delivered at other locations, such as the vestibular system, oval window, cochleostomy, etc.

For ease of illustration, FIGS. 2A and 2B have generally been described with reference to obtaining one instance of in-vivo biomarkers 250 and subsequently controlling treatment substance delivery based thereon. It is to be appreciated that, in practice, the clinical-based automated treatment substance delivery techniques presented herein may be used for extended treatment substance delivery (i.e., continuous, periodic, etc., delivery of treatment substances) over a period of time. In such arrangements, the in-vivo biomarkers 250 may be captured continuously, periodically, etc., and analyzed to quantify or assess the clinical effect thereof, in terms of pharmokinetics, concentration, toxicity, and/or efficacy, of a prior delivery of one or more treatment substances to the inner ear. Based on the results of analysis, the implant controller 242 adjusts the subsequent delivery to comply with desired/target clinical effect(s).

Figure 3:
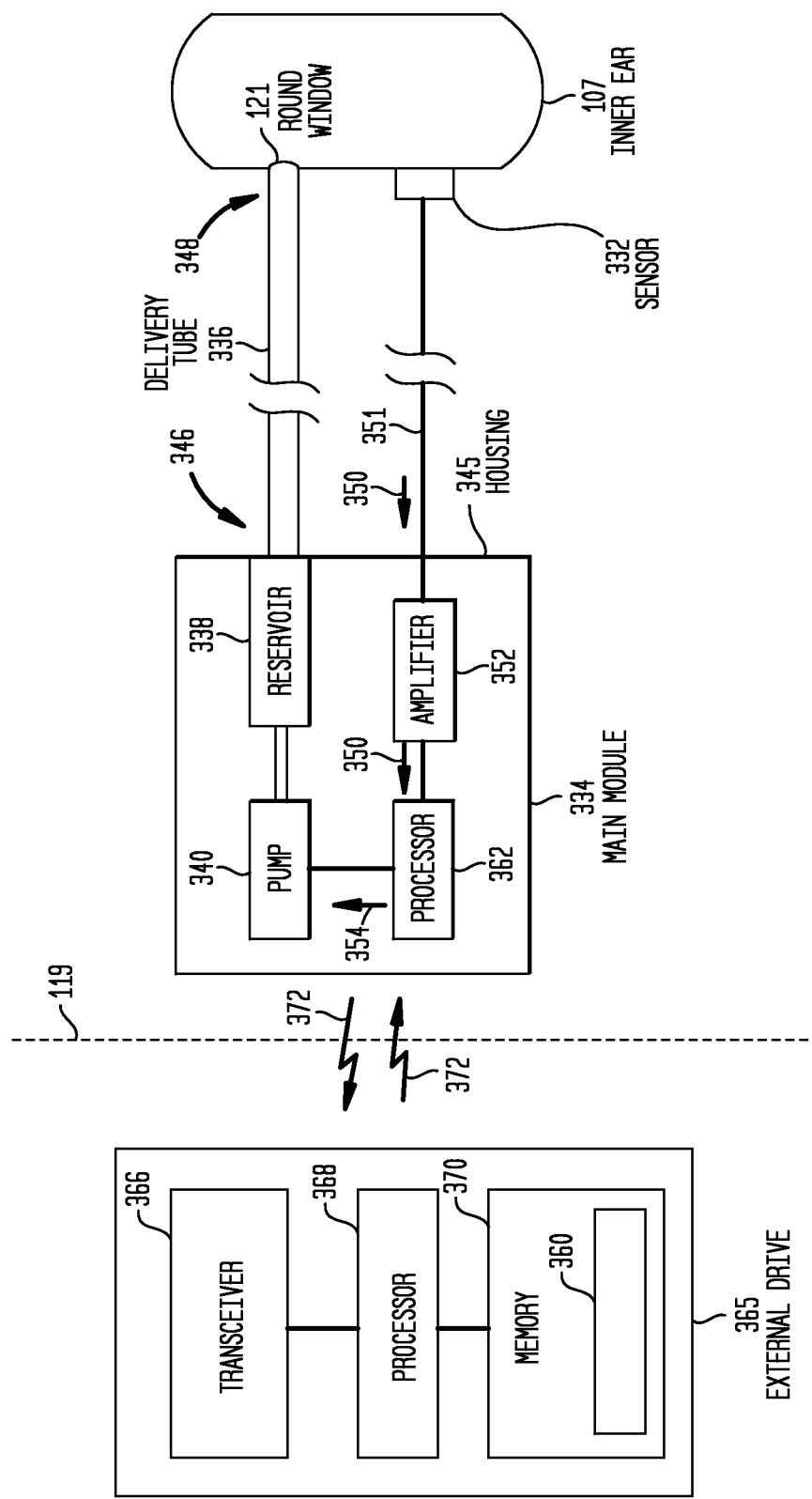
FIG. 3 is a schematic diagram of a clinical-based automated substance delivery system in accordance with certain embodiments presented herein.

In accordance with certain embodiments presented herein, the clinical-based automated (closed-loop) control of the delivery of treatment substances to the inner ear 107 may be provided by an external or remote device, rather than within the substance delivery system itself (i.e., remote control rather an on-board control). FIG. 3 is a block diagram illustrating one such arrangement for clinical-based automated remote control of the delivery of treatment substances to an inner ear of a recipient. For ease of description, the substance delivery system of FIG. 3 will be described with reference to the human anatomy of FIG. 1.

More specifically, FIG. 3 illustrates an implantable drug delivery system 300 that comprises, among other elements, one or more implantable sensors 332, an implant body (main module) 334, and a delivery tube 336. The one or more implantable sensors 332 and the delivery tube 336 may be similar to the one or more implantable sensors 232 and the delivery tube 236, respectively, described above with reference to FIGS. 2A and 2B.

The main module 334 comprises, among other elements, a reservoir 338, a pump 340, and a biological amplifier 352, all of which are disposed within a housing 345 and which may be similar to the reservoir 238, pump 240, and amplifier 252, respectively, described above with reference to FIGS. 2A-2B. As shown, the main module 334 also comprises a transceiver 362 that is configured for bi-directional wireless communication with one or more external computing devices (external devices) located external to (outside) the body of the recipient.

Also shown in FIG. 3 is one example external device 365. The external device 365 comprises, among other elements, a transceiver 366, a processor 368, and a memory 370. The memory 370 includes inner ear analysis logic 370. The external device 365 may be a device that is configured to be worn by the recipient, such as a behind-the-ear (BTE) unit (e.g., mini or micro-BTE) configured to be attached to and worn adjacent to the recipient's ear, an in-the-canal unit that is configured to be located in the recipient's ear canal, an off-the-ear headpiece (i.e., a button processor), etc. Alternatively, the external device 364 may be a remote control device (remote control), a mobile device (e.g., mobile phone, tablet computer, etc.), a computer (e.g., laptop computer, desktop computer, etc.), or other local or remote computing device (e.g., server).

In the embodiment of FIG. 3, the main module 334 is positioned within the recipient underneath a portion of the recipient's tissue 119 (e.g., between layers of the recipient's tissue 119, adjacent to a subcutaneous outer surface 229 of the recipient's skull, etc.). The reservoir 338, which is at least partially filled with a treatment substance, is fluidically coupled to the inner ear 107 via the delivery tube 336. In particular, a proximal end 346 of the delivery tube 336 is fluidically coupled to the reservoir 338, while a distal end 348 of the delivery tube 336 is fluidically coupled to the recipient's inner ear 107 and, more particularly, to the round window 121. The delivery tube 336 may be secured within the recipient so that the distal end 214 remains located adjacent to the round window 121.

The pump 340 may be, for example, an osmotic pump, infusion pump, or other type of substance delivery component/device that is activated to release a treatment substance from the reservoir 338 into the proximal end 346 of the delivery tube 336. Once released, the treatment substance travels to the distal end 348 of the delivery tube 336 for application to the inner ear 107 (e.g., the round window 121).

As noted, the main module 334 and the external device 365 include wireless transceivers 362 and 366, respectively. The wireless transceivers 362 and 366 are configured in accordance with one or more wireless technology standards to exchange data over a short distance (e.g., using short-wavelength Ultra high frequency (UHF) radio waves in one or more industrial, scientific and medical (ISM) radio bands, such as the ISM band from 2.4 to 2.485 Gigahertz (GHz)). That is, the wireless transceivers 362 and 366 provide a bi-directional wireless data link between the main module 334 and the external device 365. In FIG. 3, the bi-directional wireless data link is represented by arrows 372.

In the embodiment of FIG. 3, the sensor 332 is an electrode that is configured to capture in-vivo biomarkers, in the form of one or more in-vivo biomarkers, which are generally represented in FIG. 3 by arrow 350. The in-vivo biomarkers 350 are provided to the biological amplifier 352 via a wire/lead 351. In other words, the biological amplifier 352 is configured to measure the electrical potentials detected at the electrode 332 via wire 351. The biological amplifier 352 is configured to generate amplified version of the in-vivo biomarkers 350 and to provide the amplified in-vivo biomarkers to the transceiver 362. For ease of description, the amplified version of the in-vivo biomarkers are referred to herein simply as in-vivo biomarkers 350. The transceiver 362 is configured to wirelessly send/transmit the in-vivo biomarkers 350 to the external device 365 via the bi-directional wireless data link 372.

As noted, the external device 365 includes a transceiver 366. The transceiver 366 is configured to receive the in-vivo biomarkers 350 sent by the transceiver 362 over the bi-directional wireless data link 372. The in-vivo biomarkers 350 are then provided to the processor 368.

The in-vivo biomarkers 350 represent a biological state of one or more corresponding/associated physiological elements of the inner ear 107. In the embodiment of FIG. 3, the processor 368 is configured to analyze the in-vivo biomarkers 350, to determine a biological state of the one or more corresponding physiological elements of the inner ear 107 (i.e., the physiological elements relating to the captured in-vivo biomarkers). In certain embodiments, the biological state of the one or more corresponding physiological elements is used to quantify or assess a clinical effect, in terms of pharmokinetics, concentration, toxicity, and/or efficacy, of a prior delivery of a treatment substance to the inner ear 107. Based on the biological state of the one or more physiological elements of the inner ear (as determined by the processor 368), and possibly the assessment of the clinical effect, the processor 368 is configured to generate a "treatment substance control output" relating to the subsequent delivery of the treatment substance within reservoir 338 to the inner ear 107. The treatment substance control output(s) ensure that delivery of the treatment substances remains in a desired treatment window (i.e., is clinically effective and does not have toxic effects).

As discussed above with reference to FIGS. 2A and 2B, the type of analysis performed by the processor 368 may take a number of different forms and may depend, for example, on the in-vivo biomarkers 350 obtained from the inner ear 107. In certain embodiments, the analysis performed by the processor 368 can include, but is not be limited to, a comparison of the determined biological state of one or more physiological elements (as determined from the captured in-vivo biomarkers 350) against one or more predetermined biological states. More specifically, the determined biological state of one or more physiological elements could be compared against: a baseline measure which represents the biological state of the same one or more physiological elements of the recipient's inner ear 107 prior to delivery of a treatment substance to the inner ear (e.g., determined based on prior in-vivo biomarkers), a biological state determined based on normative data (e.g., from a normative sample of the recipient population), or other type of comparison. In such embodiments, the comparison may be absolute, frequency-based, template/pattern based (i.e., an amplitude or frequency domain operation in which the measured signals are correlated with a known template/pattern that was, for example, previously observed for the recipient, determined from normative data, etc.), or other type of comparison. It is also to be appreciated that two or more different sets of in-vivo biomarkers 350 may be combined or compared with each other to provide additional information for use by the processor 368. As noted, based on the analysis of the in-vivo biomarkers 350, the processor 368 is configured to generate an appropriate treatment substance control output. In general, the treatment substance control output may have a number of different forms. For example, in the embodiment of FIG. 3, the treatment substance control outputs comprises one or more "substance delivery control signals," represented in FIG. 3 by arrow 354. Since the processor 368 is disposed in external device 365, the substance delivery control signals 354 generated by processor 368 are first provided to the transceiver 366, then subsequently sent to the transceiver 362 over bi-directional data link 372. The transceiver 362 then provides the substance delivery control signals 354 to the pump 340. The substance delivery control signals 354 are used by the pump 340 to control/regulate (e.g., initiate, adjust, etc.) delivery of the treatment substance within reservoir 338 to the inner ear 107. The substance delivery control signals 354 may represent or define, for example, the concentration, dose, or other control parameters for the subsequent delivery of the treatment substance to the inner ear 107 of the recipient. In certain embodiments, the substance delivery control signals 354 are generated based on an assessment of the clinical effect, in terms of pharmokinetics, concentration, toxicity, and/or efficacy, of a prior delivery of a treatment substance to the inner ear 107 (i.e., the control parameters for the subsequent delivery of the treatment substance are based on the clinical effect of the prior delivery of a treatment substance to the inner ear 107). The use of the biological state of the one or more physiological elements ensures that that the subsequent delivery of the treatment substances remains in a desired treatment window (i.e., is clinically effective and does not have toxic effects).

Using the substance delivery control signals 354, operation of the pump 340 can be automatically set so that the subsequent delivery of the treatment substance to the inner ear 107 complies with the parameters set by the processor 368. Stated differently, the substance delivery control signals 354 generated by the processor 368 represent a form of closed-loop feedback that is used to auto-regulate the delivery of the treatment substance to the inner ear 107 (i.e., trigger a change in the controller of the pump 340 to, for example, increase or decrease dosage, concentration, etc. of the treatment substance delivered to the inner ear based on the biological state of the one or more physiological elements of the inner ear).

Similar to the embodiment of FIGS. 2A and 2B, the generation of substance delivery control signals 354 are an example of the treatment substance control output(s) that can be generated by the processor 368. It is to be appreciated that the processor 368 may also or alternatively generate other types of treatment substance control output(s). For example, in the same or other embodiments, the treatment substance control output(s) may comprise a signal initiating the generation of an audible or visible message/notification at the external device 365 (or other device) to the recipient, a clinician, a caregiver, or other user. The audible or visible message/notification may recommend, for example, changes to the dose or dosage of the treatment substance. Also or alternatively, the treatment substance control output(s) may comprise the generation of signals initiating the sending of a wireless notification for display, via another computing device that recommends, for example, changes to the dose or dosage of the treatment substance.

In order to analyze the in-vivo biomarkers and generate the treatment substance control output(s), as described above, the processor 368 is configured to execute software, namely inner ear analysis logic 360 stored in memory 370. The memory 370 may be ROM, RAM, or another type of physical/tangible memory storage device. Thus, in general, the memory 370 may comprise one or more tangible (non-transitory) computer readable storage media (e.g., a memory device) encoded with software comprising computer executable instructions and when the software is executed (by the one or more processors 368) it is operable to perform the operations described herein to analyze the in-vivo biomarkers and generate the treatment substance control output(s).

In summary, FIG. 3 illustrates an embodiment in which a remote device is configured to administer/control (e.g., initiating, regulating, modifying, etc.) delivery of treatment substances to the inner ear 107 based on a biological state of one or more physiological elements of the inner ear. As described above, the biological state of the one or more physiological elements of the inner ear 107 is evaluated by the processor 368 based on the in-vivo biomarkers 350 that are obtained, in-vivo, from the one or more implantable sensors 332.

Figure 4A:
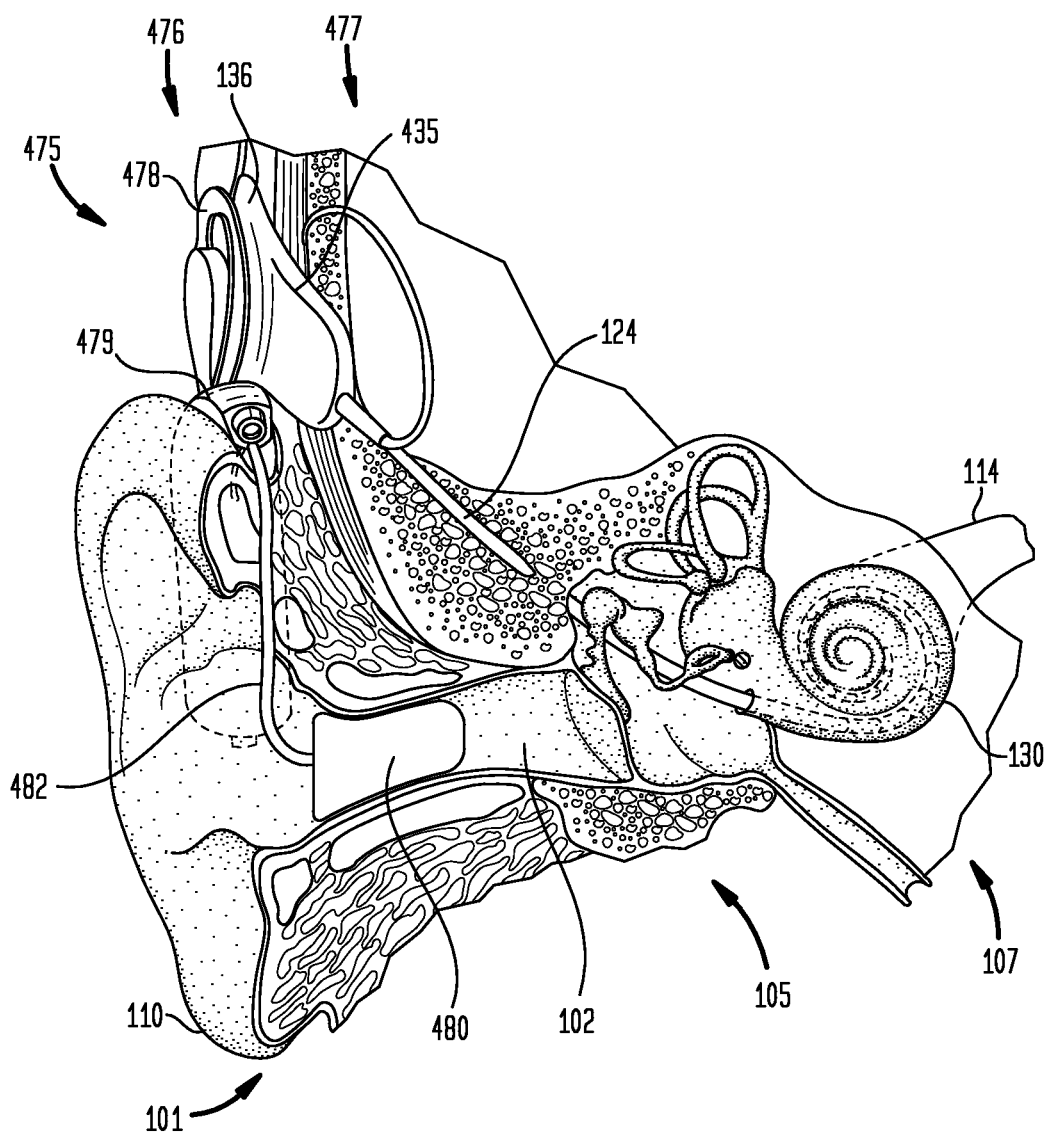
FIG. 4A is a schematic diagram of an electro-acoustic hearing prosthesis in accordance with certain embodiments presented herein.

The embodiments of FIGS. 2A, 2B, and 3 have primarily been described with reference to stand-alone treatment substance delivery systems implanted within a recipient. As noted elsewhere herein, the clinical-based automated substance delivery techniques presented herein may also be implemented by a number of different implantable medical devices, including hearing/auditory prostheses, such as cochlear implants, electro-acoustic hearing prostheses, etc. FIGS. 4A and 4B are diagrams illustrating an example electro-acoustic hearing prosthesis 475 configured to implement the clinical-based automated substance delivery techniques presented herein. For ease of description, the electro-acoustic hearing prosthesis 475 will be described with reference to the human anatomy of FIG. 1.

FIG. 4A is a schematic diagram of the electro-acoustic hearing prosthesis 475, while FIG. 4B is a block diagram of the electro-acoustic hearing prosthesis 475. The electro-acoustic hearing prosthesis 475 includes an external component 476 and an internal/implantable component 477. The external component 476 is configured to be directly or indirectly attached to the body of a recipient, while the implantable component 477 is configured to be subcutaneously implanted within the recipient (i.e., under the skin/tissue 119 of the recipient).

The external component 476 comprises an external coil 478 and a sound processing unit 479 connected via, for example, a cable 134. The external coil 478 is typically a wire antenna coil comprised of multiple turns of electrically insulated single-strand or multi-strand platinum or gold wire. Generally, a magnet (not shown in FIG. 4A) is fixed relative to the external coil 478. The external component 476 also comprises a hearing aid component 480 that includes a receiver 481 (FIG. 4B). The hearing aid component 480 is connected to the sound processing unit 479 via a cable 482. The receiver 481 is a component that is configured to deliver an acoustic signal (acoustic stimulation) to the recipient via the recipient's ear canal and middle ear. The receiver 481 may be, for example, positioned in or near the recipient's outer ear 101.

The sound processing unit 479 comprises one or more sound input elements 483 (e.g., microphones, telecoils, audio inputs, etc.), at least one processor 484, an external transceiver unit (transceiver) 485, a power source 486, and a memory 470. The memory 470 comprises inner ear analysis logic 460. The sound processing unit 479 may be, for example, a behind-the-ear ("BTE") sound processing unit or other type of processing unit worn on the recipient's head.

The implantable component 477 comprises an implant body (main module) 434, a lead region 487, and an elongate intra-cochlear stimulating assembly (electrode array) 488. The main module 434 generally comprises a hermetically-sealed housing 445 in which an internal transceiver unit (transceiver) 462 and a stimulator unit 489 are disposed. The implant body 434 also includes an internal/implantable coil 490 that is generally external to the housing 445, but which is connected to the transceiver 462 via a hermetic feedthrough (not shown in FIG. 4A or 4B). Implantable coil 490 is typically a wire antenna coil comprised of multiple turns of electrically insulated single-strand or multi-strand platinum or gold wire. The electrical insulation of implantable coil 490 is provided by a flexible molding (e.g., silicone molding), which is not shown in FIG. 4A or 4B. Generally, a magnet (not shown in FIG. 4A or 4B) is fixed relative to the implantable coil 490.

Elongate stimulating assembly 488 is configured to be at least partially implanted in the recipient's cochlea 130 (not shown in FIG. 4B) and includes a plurality of longitudinally spaced intra-cochlear stimulating electrodes 491 that collectively form an electrode array. Stimulating assembly 488 extends through an opening in the cochlea (e.g., cochleostomy, the round window, etc.) and has a proximal end connected to stimulator unit 489 via lead region 487 and a hermetic feedthrough (not shown in FIG. 4A or 4B). As such, lead region 487 couples the stimulating assembly 488 to the main module 434 and, more particularly, stimulator unit 489.

Returning to external component 476, the sound input elements 483 are configured to detect/receive sound signals and generate electrical signals therefrom. These output signals are representative of the detected sound signals. The at least one processor 484 is configured execute sound processing and coding to convert the electrical signals received from the sound input elements 483 into coded data signals that represent acoustic and/or electrical stimulation for delivery to the recipient. That is, the electro-acoustic hearing prosthesis 475 operates to evoke perception by the recipient of sound signals received by the sound input elements 483 through the delivery of one or both of electrical stimulation signals and acoustic stimulation signals to the recipient. As such, depending on a variety of factors, the at least one processor 484 is configured to convert the output signals received from the sound input elements into a first set of coded signals representative of electrical stimulation and/or into a second set of coded signals representative of acoustic stimulation. The coded signals representative of electrical stimulation are represented in FIG. 4B by arrow 415, while the coded signals representative of acoustic stimulation are represented in FIG. 4B by arrow 417.

The coded signals 415 are provided to the transceiver 485, which is configured to transcutaneously transfer the coded signals 415 to the implantable component 477 via external coil 478. More specifically, the magnets fixed relative to the external coil 478 and the implantable coil 490 facilitate the operational alignment of the external coil with the implantable coil. This operational alignment of the coils 478 and 490 enables the external coil 478 to transmit the coded data signals 415 (and power signals) from the external component 476 to the implantable component 477, and vice versa. That is, the operational alignment of the coils 478 and 490 the formation of a bi-directional data link that enables the transfer of data between the external component 476 and the implantable component 477. In FIG. 4B, the directional data link is generally represented by arrows 472.

In certain examples, the external coil 478 and the implantable coil 490 communicate via a radio frequency (RF) link. However, various other types of energy transfer, such as infrared (IR), electromagnetic, capacitive and inductive transfer, may be used to transfer the power and/or data from an external component to an electro-acoustic hearing prosthesis and, as such, FIG. 4B illustrates only one example arrangement of a bi-directional data link 471 that enables the transfer of data between the external component 476 and the implantable component 477.

Returning to the specific arrangement of FIG. 4B, the coded data signals 415 sent over directional data link 471 are received at the transceiver 462 and provided to the stimulator unit 489. The stimulator unit 489 is configured to utilize the coded data signals 415 to generate stimulation signals (e.g., current signals) for delivery to the recipient's cochlea via one or more stimulating contacts 491. In this way, electro-acoustic hearing prosthesis 475 stimulates the recipient's auditory nerve cells, bypassing absent or defective hair cells that normally transduce acoustic vibrations into neural activity, in a manner that causes the recipient to perceive the received sound signals.

Certain hearing prosthesis recipients may retain some normal hearing functionality (i.e., retain at least some residual hearing). Therefore, the cochlea 130 of certain hearing prosthesis recipients can be acoustically stimulated upon delivery of a sound signal to the recipient's outer ear 101, with the aid of the hearing prosthesis itself or, in certain cases, without the aid of the hearing prosthesis. In the example of FIGS. 4A and 4B, the receiver 481 is used to aid the recipient's residual hearing. More specifically, the coded signals 417 (i.e., the signals representative of acoustic stimulation) are provided to the receiver 481. The receiver 481 is configured to utilize the coded signals 417 to generate the acoustic stimulation signals that are provided to the recipient. In other words, the receiver 481 is used to enhance, and/or amplify a sound signal which is delivered to the cochlea via the middle ear bones and oval window, thereby creating dynamic pressure changes in the perilymph within the cochlea.

In addition to the ability to electrically and acoustically stimulate the inner ear 107 of the recipient, the electro-acoustic hearing prosthesis 475 is also configured to deliver treatment substances to the inner ear 107 of the recipient. More specifically, in the example of FIGS. 4A and 4B, the stimulating assembly 488 includes one or more substance-eluting portions 492 that, when activated, are configured to release a treatment substance into the inner ear 107. In certain embodiments, the substance-eluting portions 492 can be activated in response to application of electrical fields thereto. The electrical fields that activate the substance-eluting portions 492 can be applied by the electrodes 491, one or more extra cochlear electrodes (not shown), etc. In certain embodiments, the one or more substance-eluting portions 492 are formed of charge activated biodegradable polymers, smart polymers, etc., capable of responding to changing electric fields.

As noted above, the clinical-based automated substance delivery techniques utilize one or more implantable sensors to capture in-vivo biomarkers representing the biological state of one or more corresponding physiological elements of the inner ear 107. In the embodiment of FIGS. 4A and 4B, the intra-cochlear electrodes 491 operate as the sensors to capture in-vivo biomarkers in the form of in-vivo biomarkers. In FIG. 4B, the in-vivo biomarkers are generally represented by arrow 450.

The stimulator unit 489 includes a biological amplifier 452 that is connected to the electrodes 491 via one or more wires/lead (not shown on FIG. 4B) disposed in the stimulating assembly 488 and/or the lead region 487. The biological amplifier 452 is configured to measure the electrical potentials detected at the electrodes 491 and, in response, generate electrical input signals. The electrical input signals generated by the biological amplifier 452 are amplified versions of the in-vivo biomarkers 450 and, for ease of description, are referred to herein simply as in-vivo biomarkers 450. The biological amplifier 452 is configured to provide the in-vivo biomarkers 450 to the transceiver 462. The transceiver 462 is configured to wirelessly send/transmit the in-vivo biomarkers 450 to the sound processing unit 479 via the bi-directional wireless data link 472.

As noted, the sound processing unit 479 includes a transceiver 485. The transceiver 485 is configured to receive the in-vivo biomarkers 450 sent by the transceiver 462 over the bi-directional wireless data link 472. The in-vivo biomarkers 450 are then provided to the at least one processor 484.

As noted, the in-vivo biomarkers 450 represent a biological state of one or more corresponding physiological elements of the inner ear. In the embodiment of FIGS. 4A and 4B, at least one of the processors 484 is configured to analyze the in-vivo biomarkers 450 to determine a biological state of the one or more corresponding physiological elements of the inner ear 107 (i.e., the physiological elements relating to the captured in-vivo biomarkers). Based on the biological state of the one or more physiological elements of the inner ear 107 (as determined by the at least one processor 484), the processor 484 is configured to generate one or more "treatment substance control outputs" relating to the subsequent delivery of a treatment substance to the inner ear 107. The treatment substance control output(s) ensure that delivery of the treatment substances remains in a desired treatment window (i.e., is clinically effective and does not have toxic effects).

As discussed above with reference to FIGS. 2A and 2B, the type of analysis performed by the at least one processor 484 may take a number of different forms and may depend, for example, on the obtained in-vivo biomarkers 450. In certain embodiments, the analysis performed by the at least one processor 484 can include, but is not be limited to, a comparison of the determined biological state of one or more physiological elements (as determined from the captured in-vivo biomarkers 450) against one or more predetermined biological states. More specifically, the determined biological state of one or more physiological elements could be compared against: a baseline measure which represents the biological state of the same one or more physiological elements of the recipient's inner ear 107 prior to delivery of a treatment substance to the inner ear (e.g., determined based on prior in-vivo biomarkers), a biological state determined based on normative data (e.g., from a normative sample of the recipient population), or other type of comparison. In such embodiments, the comparison may be absolute, frequency-based, template/pattern based (i.e., an amplitude or frequency domain operation in which the measured signals are correlated with a known template/pattern that was, for example, previously observed for the recipient, determined from normative data, etc.), or other type of comparison. It is also to be appreciated that two or more different sets of in-vivo biomarkers may be combined or compared with each other to provide additional information for use by the at least one processor 484.

As noted, based on the analysis of the in-vivo biomarkers 450, the at least one processor 484 is configured to generate an appropriate treatment substance control output. In general, the treatment substance control output may have a number of different forms. For example, in the embodiment of FIGS. 4A and 4B, the treatment substance control outputs comprise one or more "substance delivery control signals," represented in FIG. 4B by arrow 454. Since the at least one processor 484 is disposed in sound processing unit 479, the substance delivery control signals 454 generated by the at least one processor 484 are sent to the implantable component 477 over bi-directional data link 472. The transceiver 462 then provides the substance delivery control signals 454 to the substance delivery component, which in this example comprises stimulator 489. The stimulator 489 uses the substance delivery control signals 454 to control/regulate (e.g., initiate, adjust, etc.) delivery of the treatment substance within stimulating assembly 488 to the inner ear 107. More specifically, based on the substance delivery control signals 454, the stimulator unit 489 generates one or more electrical fields (e.g., via electrodes 491) which activate one or more substance-eluting portions 492 to, accordingly, release a treatment substance into the inner ear 107. The electrical fields are generated to, for example, increase or decrease in the activation of a region of the stimulating assembly 488 (e.g., by decreasing/increasing the local charge at specific substance-eluting portions 492).

The substance delivery control signals 454 may represent or define, for example, the concentration, dose, or other control parameters for the subsequent delivery of the treatment substance to the inner ear 107 of the recipient. In certain embodiments, the substance delivery control signals 454 are generated based on an assessment of the clinical effect, in terms of pharmokinetics, concentration, toxicity, and/or efficacy, of a prior delivery of a treatment substance to the inner ear 107 (i.e., the control parameters for the subsequent delivery of the treatment substance are based on the clinical effect of the prior delivery of a treatment substance to the inner ear 107).

Using the substance delivery control signals 454, the stimulator unit 489 automatically sets parameters of the electric field(s) to achieve a substance release that complies with the parameters set by the at least one processor 484. Stated differently, the substance delivery control signals 454 generated by the at least one processor 484 represent a form of closed-loop feedback that is used to auto-regulate the delivery of the treatment substance to the inner ear 107 (i.e., trigger a change in the stimulator unit 489 to, for example, increase or decrease dosage, concentration, etc. of the treatment substance delivered to the inner ear based on the biological state of the one or more physiological elements of the inner ear).

Similar to the embodiment of FIGS. 2A and 2B, the generation of substance delivery control signals 454 are an example of the treatment substance control output(s) that can be generated by the at least one processor 484. It is to be appreciated that the at least one processor 484 may also or alternatively generate other types of treatment substance control output(s). For example, in the same or other embodiments, the treatment substance control output(s) may comprise a signal initiating the generation of an audible or visible message/notification (e.g., at the sound processing unit 479 or other external device) to the recipient, a clinician, a caregiver, or other user. The audible or visible message/notification may recommend, for example, changes to the dose or dosage of the treatment substance. Also or alternatively, the treatment substance control output(s) may comprise the generation of signals initiating the sending of a wireless message for display, via another computing device that recommends, for example, changes to the dose or dosage of the treatment substance.

In order to analyze the in-vivo biomarkers and generate the treatment substance control output(s), as described above, the at least one processor 484 is configured to execute software, namely inner ear analysis logic 460 stored in memory 470. The memory 470 may be ROM, RAM, or another type of physical/tangible memory storage device. Thus, in general, the memory 470 may comprise one or more tangible (non-transitory) computer readable storage media (e.g., a memory device) encoded with software comprising computer executable instructions and when the software is executed (by the at least one processor 484) it is operable to perform the operations described herein to analyze the in-vivo biomarkers and generate the treatment substance control output(s).

In summary, FIGS. 4A and 4B illustrate an embodiment in which a hearing prosthesis is configured to administer/control (e.g., initiating, regulating, modifying, etc.) delivery of treatment substances to the inner ear 107 based on a biological state of one or more physiological elements of the inner ear. As described above, the biological state of the one or more physiological elements of the inner ear 107 is evaluated by the at least one processor 484 based on the in-vivo biomarkers 450 that are obtained, in-vivo, from the one or more implantable sensors (e.g., electrodes 491).

FIGS. 4A and 4B illustrate one example arrangement for the electro-acoustic hearing prosthesis 475. However, it is to be appreciated that embodiments of the present invention may be implemented in electro-acoustic devices having alternative arrangements and/or in other types of hearing prostheses comprising different types of output devices (e.g., receivers, direct acoustic stimulators, bone conduction devices, intra-cochlear stimulating assemblies, auditory brain implants, etc.). In addition, it is to be appreciated that embodiments of the present invention may be implemented in totally implantable medical device, such as a totally implantable cochlear implant. A totally implantable medical device is a medical device in which all components of the device are configured to be implanted under the skin/tissue of a recipient. Because all components are implantable, the totally implantable medical device operates, for at least a finite period of time, without the need of an external device. In such embodiments, an external device can be used to, for example, charge the internal power source (battery).

FIGS. 2A, 2B, 3, 4A, and 4B illustrate several treatment substance mechanisms that may be controlled using the clinical-based automated treatment substance delivery techniques presented herein. It is to be appreciated that the above described delivery mechanisms illustrative and that the techniques presented herein may be used to control any of a number of other delivery mechanisms or substance delivery components etc., including other controlled release systems/mechanisms, sustained release systems/mechanisms, systemic deliveries mechanisms (e.g., oral, injection, pump, etc.), intra-tympanic injections (middle ear injections), etc.

FIG. 5 is a flowchart illustrating a clinical-based automated treatment substance delivery method 595 in accordance with embodiments presented herein. Method 595 begins at 596 where at least one implantable sensor captures in-vivo biomarkers associated with physiological elements of an inner ear of a recipient of an implantable medical device. At 597, at least one processor analyzes the in-vivo biomarkers to determine a biological state of the one or more physiological elements of the inner ear associated with the in-vivo biomarkers. At 598, based on the biological state of the one or more corresponding physiological elements of the inner ear, the at least one processor generates a treatment substance control output characterizing subsequent delivery of one or more treatment substances to the inner ear of the recipient.

It is to be appreciated that the clinical-based automated treatment substance delivery techniques presented herein may be used to treat a number of inner ear disorders. Provided below is a table illustrating several example use cases in which the clinical-based automated treatment substance delivery techniques may be implemented to treat an inner ear disorder. It is it be appreciated that the specific use cases provided below are illustrative of the many use cases for the clinical-based automated treatment substance delivery techniques presented herein.

| Treatment, Disorder, or Pathology | Treatment Substance Type or Therapy | Applicable In-vivo biomarker(s) and Treatment Summary |
|---|---|---|
| Ménière's Disease | Triamterene (diuretic) Meclizine (anti-vertigo) Diazepan (vertigo - see vestibular imbalance, below) Promethazine (anti-nausea) | Efficacy of the diuretic can be monitored by calculating the ratio of the summating potential (SP) and compound action potential (AP). Changes in this ratio reveal that a change to the 'bowing' of the scala media cause by hydrops (related to Meniere's disease). Vertigo treatments (see vestibular imbalance and suppressants below). The anti-vertigo (and anti-nausea) treatments work by blocking certain chemicals in the brain. One such example is the blocking of dopamine in the brain. Changes to the dopaminergic pathways can be detected by monitoring the electroencephalographic (EEG) changes using the implant whereby electrodes are placed near the brain. Changes are observed in the power spectra tagged as delta, theta, alpha, beta and gamma with respects to a known baseline. |
| Inflammatory Response | Steroids | Steroids can be provided both during surgery and during episodes of diagnosed dizziness and or middle ear infections. The efficacy of the steroid may be assess via an impedance in-vivo biomarker that reflects changes in the biological content of the scala tympani or vestibular system where the electrode contact or array is positioned. |
| Reparative and Regenerative treatments | Gene therapies | Pathologies involving hair cell loss will involve therapies that seek to repair or regenerate hair cells by manipulating cell proliferation control. The ECoG is a means of monitoring the location and density of this HC regeneration by characterising the CM magnitude across a number of frequencies involved in human audition. When applied to auditory nerve preservation and fiber regeneration the neural components of the ECoG response, CAP and ANN, can be used to monitor the proliferation, density and longevity of such preservative and regenerative therapies. The magnitude, morphology and frequency response of the CAP and ANN can be used as markers. |
| Age-related sensorineural hearing loss (presbycusis) | Neurotrophins (e.g., brain derived neurotrophic factors) | These are preventive therapies and much like the gene therapies, target the spiral ganglion neurons in an effort to slow or cease the sensorineural hearing loss with age. May use similar in-vivo biomarkers as described above with reference to gene therapies. |
| Vestibular imbalance | Vestibular suppressants | Vestibular suppressants generally reduce nystagmus (eye movements) cause by vestibular imbalance. By monitoring the vestibular nerve or the hair cell activity within the vestibular system it is possible to track the magnitude of the nystagmus. |
| Otoprotective Agents | Drugs for noise and drug induced ototoxicity (e.g., D-met) | See methodology described by the Regenerative and Reparative treatments |

It is to be appreciated that the embodiments presented herein are not mutually exclusive.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical device system, comprising:
    at least one sensor configured to be implanted in an inner ear of a recipient;
    an implantable reservoir configured to hold a treatment substance; and
    at least one processor configured to:
        obtain, via the at least one sensor, an electrophysiological measurement from the inner ear of the recipient;
        control, using the electrophysiological measurement for feedback, delivery of the treatment substance from the implantable reservoir;
        detect at least one of hair cell changes or synaptic changes from the electrophysiological measurement; and
        auto-regulate an amount of the treatment substance delivered to the inner ear responsive to the at least one of hair cell changes or synaptic changes;
    a stimulating assembly configured to be implanted in the inner ear, wherein the stimulating assembly includes the at least one sensor as one or more electrodes configured to detect the electrophysiological measurement as electrical potentials; and
    an amplifier connected to the one or more electrodes, wherein the amplifier is configured to amplify the electrical potentials detected at the one or more electrodes for use by the at least one processor,
        wherein the implantable medical device system is configured to sample the electrical potentials detected at the one or more electrodes during a fixed duration measurement window following at least one of electrical stimulation or acoustic stimulation.

2. The implantable medical device system of claim 1, wherein the at least one sensor comprises one or more intra-cochlear electrodes of a cochlear implant.

3. The implantable medical device system of claim 1, wherein the at least one sensor comprises one or more electrodes of a vestibular implant.

4. The implantable medical device system of claim 1, wherein the electrophysiological measurement comprises one or more electrically evoked compound action potential (ECAP) measurements.

5. The implantable medical device system of claim 1, further comprising:
    a pump configured to deliver the treatment substance from the implantable reservoir to the inner ear of the recipient.

6. The implantable medical device system of claim 1, wherein the implantable medical device system is configured to record a voltage waveform detected at the one or more electrodes during the fixed duration measurement window.

7. The implantable medical device system of claim 6, wherein the implantable medical device system is configured to determine changes in a power spectrum density of the voltage waveform.

8. The implantable medical device system of claim 1, wherein the at least one processor is configured to:
    initiate generation of at least one acoustic stimulus configured to evoke a neural response associated with an auditory nerve of the recipient.

9. The implantable medical device system of claim 1, wherein the electrophysiological measurement comprises one or more electrocochleography (ECoG) measurements.

10. A method, comprising:
    delivering an electrical stimulus to an inner ear of a recipient of an implantable medical device;
    capturing, via at least one implantable sensor, one or more electrophysiological measurements as an electrically evoked compound action potential measurement from the inner ear during a fixed duration sample window that immediately follows the electrical stimulus; and
    using the one or more electrophysiological measurements as feedback, generating a control output to auto-regulate delivery of one or more treatment substances to the inner ear of the recipient.

11. The method of claim 10, further comprising delivering, via the implantable medical device, the one or more treatment substances to the inner ear of the recipient.

12. The method of claim 11, further comprising auto-regulating an amount of the one or more treatment substances delivered to the inner ear of the recipient dependent on the control output.

13. The method of claim 10, further comprising calculating a dosage of the one or more treatment substances dependent on the one or more electrophysiological measurements.

14. The method of claim 13, further comprising decreasing an amount of the one or more treatment substances delivered to the inner ear of the recipient responsive to the dosage.

15. The method of claim 10, further comprising:
    delivering an acoustic stimulus to the inner ear of the recipient of the implantable medical device; and
    capturing the one or more electrophysiological measurements as an acoustically evoked electrophysiological measurement from the inner ear of the recipient via the at least one implantable sensor during an additional fixed duration sample window that immediately follows the acoustic stimulus.

16. The method of claim 10, further comprising:
    detecting changes in auditory nerve function or vestibular nerve function from the one or more electrophysiological measurements; and
    modulating the control output responsive to the changes in auditory nerve function or vestibular nerve function.

17. The method of claim 10, further comprising administering the one or more treatment substances to the inner ear to regulate homeostasis responsive to detection of cell apoptosis in the one or more electrophysiological measurements.

18. The method of claim 10, further comprising estimating at least one of spiral ganglion density or spiral ganglion survival from the one or more electrophysiological measurements.

19. The method of claim 10, further comprising controlling an implantable pump dependent on the control output to auto-regulate delivery of the one or more treatment substances to the inner ear of the recipient.

20. An implantable medical device system, comprising:
    at least one sensor configured to be implanted in an inner ear of a recipient;
    an implantable reservoir configured to hold a treatment substance; and
    at least one processor configured to:
        obtain, via the at least one sensor, an electrophysiological measurement from the inner ear of the recipient;

estimate at least one of spiral ganglion density or spiral ganglion survival from the electrophysiological measurement; and control, using the electrophysiological measurement for feedback, delivery of the treatment substance from the implantable reservoir.

21. The implantable medical device system of claim 20, wherein the at least one sensor comprises one or more intra-cochlear electrodes of a cochlear implant.

22. The implantable medical device system of claim 20, wherein the at least one sensor comprises one or more electrodes of a vestibular implant.

23. The implantable medical device system of claim 20, wherein the at least one processor is configured to auto-regulate delivery of the treatment substance to the recipient responsive to changes in the electrophysiological measurement obtained by the at least one sensor.

24. The implantable medical device system of claim 20, wherein the electrophysiological measurement comprises one or more electrically evoked compound action potential (ECAP) measurements.

25. The implantable medical device system of claim 20, further comprising a pump configured to deliver the treatment substance from the implantable reservoir to the inner ear of the recipient, wherein the at least one processor is configured to control a rate at which the pump delivers the treatment substance to the inner ear of the recipient responsive to the feedback.

26. The implantable medical device system of claim 20, further comprising:

a stimulating assembly configured to be implanted in the inner ear, wherein the stimulating assembly includes the at least one sensor as one or more electrodes configured to detect the electrophysiological measurement as electrical potentials; and an amplifier connected to the one or more electrodes, wherein the amplifier is configured to amplify the electrical potentials detected at the one or more electrodes for use by the at least one processor.

27. The implantable medical device system of claim 26, wherein the implantable medical device system is configured to sample the electrical potentials detected at the one or more electrodes during a fixed duration measurement window following at least one of electrical stimulation or acoustic stimulation.

28. The implantable medical device system of claim 27, wherein the implantable medical device system is configured to record a voltage waveform detected at the one or more electrodes during the fixed duration measurement window.

29. The implantable medical device system of claim 27, wherein the at least one processor is configured to detect at least one of hair cell changes or synaptic changes from the electrophysiological measurement, and auto-regulate an amount of the treatment substance delivered to the inner ear responsive to the at least one of hair cell changes or synaptic changes.

30. The implantable medical device system of claim 20, wherein the electrophysiological measurement comprises an electrocochleography (ECOG) measurement.

* * * * *